United States Patent [19]

Seney

[11] Patent Number: 4,646,735

[45] Date of Patent: Mar. 3, 1987

[54] PAIN-ALLEVIATING TISSUE TREATMENT ASSEMBLY

[76] Inventor: John S. Seney, Box 152, Sugarloaf Key, Fla. 33044

[21] Appl. No.: 784,135

[22] Filed: Oct. 4, 1985

[51] Int. Cl.[4] .................................................. A61B 17/36
[52] U.S. Cl. .......................... 128/303.1; 128/DIG. 27
[58] Field of Search .................... 128/303.1, 399–402, 128/DIG. 27; 62/93, 172, 259.3, 293, 514 R

[56] References Cited

U.S. PATENT DOCUMENTS

| | | | |
|---|---|---|---|
| 1,965,424 | 7/1934 | Mascolo | 128/402 |
| 2,672,032 | 5/1954 | Towse | 128/303.1 |
| 3,393,679 | 7/1968 | Crump et al. | 62/293 |
| 3,483,869 | 12/1969 | Hayhurst | 128/303.1 |
| 3,548,829 | 12/1970 | Reynolds | 62/514 |
| 3,794,039 | 2/1974 | Kollner et al. | 128/303.1 |
| 3,924,628 | 12/1975 | Droegemueller et al. | 128/401 |
| 3,971,383 | 7/1976 | Van Gerven | 128/303.1 |
| 4,184,537 | 1/1980 | Sauder | 128/400 |
| 4,207,897 | 6/1980 | Lloyd et al. | 128/303.1 |
| 4,211,231 | 7/1980 | Rzasa | 128/303.1 |
| 4,237,696 | 12/1980 | Coblentz | 62/93 |
| 4,275,734 | 6/1981 | Mitchiner | 128/303.1 |
| 4,280,499 | 7/1981 | Squazzi | 128/303.1 |
| 4,367,743 | 1/1983 | Gregory | 128/303.1 |
| 4,459,822 | 7/1984 | Pasternack | 62/259.3 |

*Primary Examiner*—Edward M. Coven
*Assistant Examiner*—Max F. Hindenburg
*Attorney, Agent, or Firm*—John Cyril Malloy

[57] ABSTRACT

An assembly which incorporates a hand-held instrument or device collectively structured to alleviate pain during minor surgical application wherein the operating instrument and/or the surgical site are concurrently cooled to a substantially reduced temperature. The surgical site is gently blanketed with cold, dry sterilized air, gases or other atomized treatment fluid serving to effectively reduce the temperature of the tissue at the surgical site while at the same time preventing possible room air-borne contamination entering the treatment site based on the air or gas blanketing the treatment site being sterilized or otherwise medicinally treated.

16 Claims, 4 Drawing Figures

PAIN-ALLEVIATING TISSUE TREATMENT ASSEMBLY

BACKGROUND OF THE INVENTION

1. Field of the Invention

An assembly is structured to alleviate pain from tissue at a surgical site through the reduction of temperature of the surgical instrument including a needle, scalpel, etc. and concurrently blanketing the tissue surrounding the surgical site with dry, sterilized air, gas or atomized treatment fluid also of substantially reduced temperature. Such reduced temperature fluid may also be directed to an open sore to facilitate healing when a surgical instrument is not being utilized.

2. Description of the Prior Art

In the medical profession and in the field of anesthesiology, it is well recognized that when performing minor surgery, the common accepted principles of pain reduction mechanics have been utilized for many years. More specifically, sensory nerves are associated with chemicals which combine and react according to the applied stimuli. Dependent upon this stimuli, a reaction results causing an electrical shift of the polarization of the neuron or nerve which is transmitted as pain or appropriate sensation. Because the above reaction is basically a chemical reaction, such reaction follows and obeys the general rule for stimuli activated reaction which acknowledges that the reaction rate doubles for each 10 degrees centigrade temperature increase.

This accepted principle has been used for years by surgeons and technicians in the medical profession in applying local anethesia for minor surgery. Typically, liquids such as ethyl chloride is sprayed directly on the tissue surrounding or involved in the surgical site. Substantial cooling of the tissue results in an accompanying anesthetic effect. Disadvantages associated with this basic technique are the requirement of the surgeon to stop operating and "recool" the tissue surrounding the surgical site each time such tissue increases in temperature. This technique not only takes time but allows possible room, air-borne infectious agents to enter the exposed tissue.

The prior art contains numerous patents relating generally to the concept of reducing the temperature of surgical instruments during the performance of surgical techniques and like applications. Such patents include Reynolds, U.S. Pat. No. 3,548,829; Peters, U.S. Pat. No. 3,494,364; Hirschorn, U.S. Pat. No. Re. 26,276; Gregory, U.S. Pat. No. 4,367,743; Kandbar, U.S. Pat. No. 3,259,131; Zobac, U.S. Pat. No. 4,345,598; Kollner, U.S. Pat. No. 3,794,039; and Loyd, U.S. Pat. No. 4,207,897. While the structures and systems disclosed in the patents set forth above are assumed to be operative for their intended function and application, none of the structures disclosed demonstrate a ability to direct a soothing blanket of sterile, cooled air over the exposed tissue involved in the surgical site and none include specific advantages such as maintaining a relatively warmer air pocket of forced fluid flow between an evaporator structure and an outer casing of the instrument held by the surgeon in order to prevent the substantially reduced temperature from affecting holding or gripping of the instrument.

SUMMARY OF THE INVENTION

The present invention relates to a pain alleviating assembly which is capable of generating a continuous low temperature blanket of air over tissue surrounding or involved in a site of medical care on a patient. Alternately, atomized treatment fluid may be continuously generated so as to facilitate in the healing of sores or the like. The instrumentation of the subject assembly is further structured for supporting attachment of specific surgical instruments such as a scalpel, needle, etc. so as to reduce the temperature of the instrument during surgical application.

The subject assembly comprises a micro-refrigerating evaporator built into a hand piece capable of being gripped and applied by a surgeon or like technician. The hand piece is flexibly connected to a refrigerant supply. The evaporator and hand piece are specifically structured and dimensioned to fit comfortably in the user's hand while having an operative capacity of approximately 108 BTU per hour reat removal while reaching a temperature of approximately $-20$ F ($-28.43°$ C.) with a back pressure of 0-LB gage (0-KG/SQ CM.) on the low side of the evaporator using a refrigerant such as Freon 12.

A cabinet or console is attaohed by a flexible connection defining fluid communication between the hand piece and the console. The cabinet or console contains a recirculating refrigerant supply system including a compressor, condensor and liquid refrigerant (Freon) electronic controlled flow valve. The flow valve is controlled by a temperature sensor located in the hand piece serving to sense the temperature of the evaporator structure. For protection from the reduced temperature of the evaporator in the hand piece, it is jacketed or covered by a plastic or like material casing. The space between the casing and the evaporator structure contains a forced flow of sterilized air therethrough which travels along the outer surface of the evaporator and as a result has its temperature lowered considerably. At the outer end of the hand piece and in communication with the spacing between the hand piece and the evaporator, a plurality of small slots exit this spacing and the air contained therein in a channelled or directed flow to the exterior of the hand piece and onto a tissue site. An instrument such as a scalpel, needle, etc. is attachable to the evaporator so as to extend outwardly therefrom through the plastic case. Its direct interconnection with the evaporator serves to effectively lower the temperature of the instrument close to that of the evaporator itself.

The spacing between the jacket or cover and the evaporator communicates with a flexible conduit which in turn is connected directly to the cabinet or console including the refrigerant supply. In addition, a continuous flow of sterilized air, gas, etc. is supplied from the cabinet through the conduit at a rate of approximately 1100 cubic centimers a minute. This fluid is cooled by direct contact with the exterior surface of the evaporator and exits directly around the attached surgical instrument, as set forth above, at a temperature of approximately 24° F. or $-4°$ C. This forced fluid flow cools and blankets the tissues being treated and as an anesthetic affect thereon. In order to keep the surgical site sterilized, the forced fluid supply in one example being atmospheric air, is passed through a heater assembly located in the console or cabinet. The air supply is in fluid communication with the heater assembly and accordingly the air being supplied to the hand piece is first heated to a temperature of approximately 800° F. This extreme temperature sterilizes the air prior to it reaching the hand piece. During its forced travel, the air is cooled to ambient temperature and subsequently passed into a cold heat exchanger having approximately −20° F. and −28° C. cooling surfaces. This latter heat exchanger serves to freeze the moisture out of the air to nearly zero percent humidity. A pressure regulator and a flow meter provide exact flow control of the treated air to the hand piece.

Another feature of the present invention is the ability to remove the surgical instrument, such as a scalpel, needle, etc., from the end of the evaporator along with an end cap secured to the hand piece over the end of the evaporator. A similarly structured cap replaces the surgical instrument and includes an outwardly extending nozzle or funnel designed and configured to confine and seal off the treatment area from atmosphere, and apply a controlled positive pressure healing atmosphere of temperature controlled sterile air or gas inside the funnel and over the sore. The funnel, attached to the hand piece can be hand-held or otherwise attached by numerous means to the patient directly so that the hand piece and funnel are supported in the aforementioned position and capable of being maintained in such position for treating hard to heal sores requiring extended continuous treatment. The cabinet includes a connection facility to supply treated fluid other than air to the cabinet and eventually to the hand piece.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which.

DETAILED DESCRIPTION OF THE PREFERRED EMBODIMENT

Figure 1:
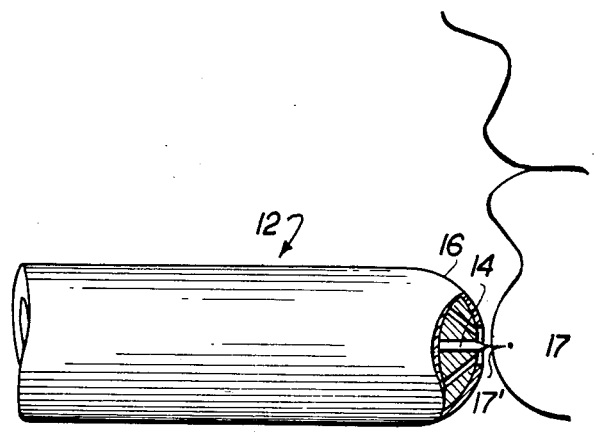
FIG. 1 is a front plan view in partial cutaway and section showing application of a hand piece portion of the subject assembly to a surgical site such as in electrolysis or the removal of hair.
Figure 2:
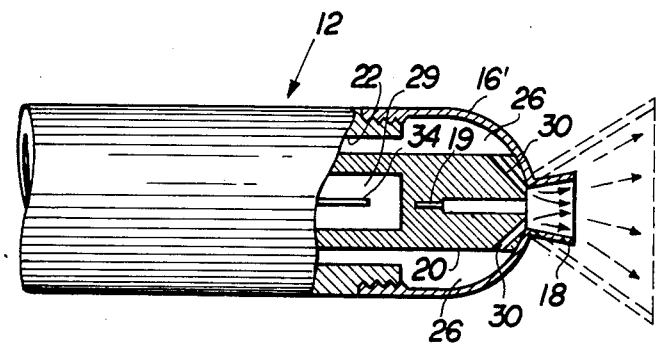
FIG. 2 is another embodiment of a hand piece assembly as shown in FIG. 1 wherein a surgical instrument is not applied but a forced flow of cool, sterilized gas or atomized fluid is directed onto tissue surrounding or involved in a surgical site.
Figure 3:
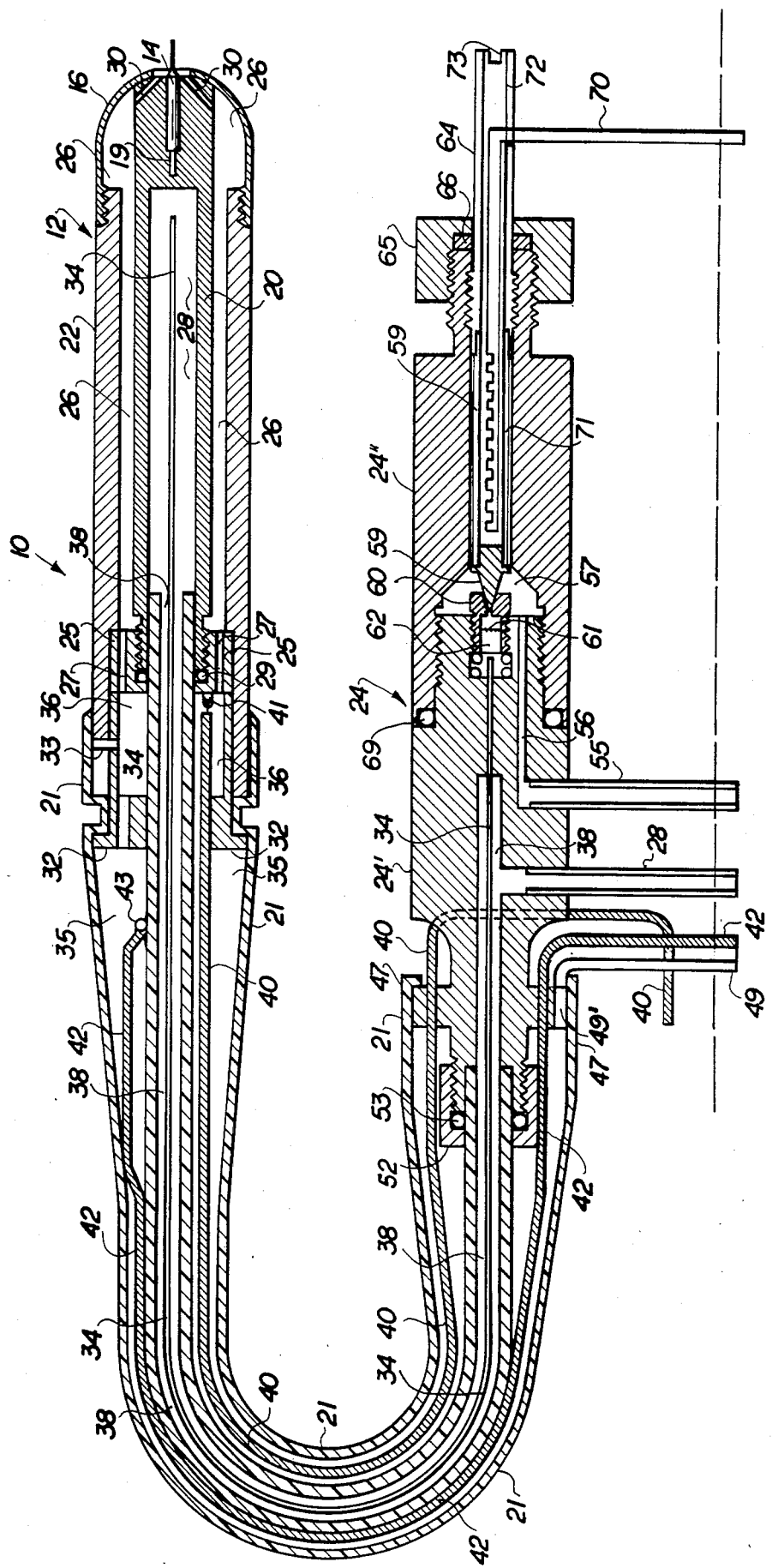
FIG. 3 is an interior sectional view of a hand piece, connecting conduit and valve body of the subject invention.

As shown primarily in FIGS. 1, 2 and 3, the assembly of the present invention is generally indicated as 10 and includes a hand piece generally indicated as 12. The use and application of the assembly of the present invention is generally shown in FIGS. 1 and 2 wherein the hand piece 12 has a surgical tool 14 such as a needle or the like, projecting outwardly from an end cap 16 and applied directly to tissue 17 of a patient for a specific purpose. In the embodiment of FIG. 1, the needle instrument 14 is used for the removal of hair 18 by electrolysis, a technique well known in the medical profession. However, in the embodiment of FIG. 2, the hand piece 12 has a modified end cap 16' secured thereto such that an endmost nozzle 18 is particularly configured and dimensioned to direct forced flow of cooled air or like fluid outwardly into contact with a specific area of tissue. The embodiment of FIG. 2 is particularly applicable wherein hard to heal sores are treated with medicated atomized fluid or like substance by direct bathing or blanketing of the sore with the fluid in the manner shown in FIG. 2.

With reference to FIG. 3, the hand piece 12 is represented as encompassing a surgical instrument 14 such as a needle. However, it should be apparent, from the description set forth hereinafter, that the important features of the assembly are such as to be operative with either of the embodiments of FIGS. 1 and 2.

With specific reference to FIG. 3, the electrolysis needle or surgical instrument 14 is mounted in a split chuck 19 which is integrally formed or otherwise connected in direct engagement with an evaporator body 20 specifically shown to be of sufficient size for mounting in hand piece 12. An end cap 16 is threadedly connected to an exteriorly disposed outer cover or casing 22 made from a plastic or like substantially heat insulating material. Threaded engagement of the end cap on the distal end of the cover 22 plus its engagement at the distal end of the evaporator body 20 serves to force the split chuck 19 into fixed engagement about the needle or like surgical instrument 14. It should be noted however that other surgical instruments can be utilized such as a scalpel or like instrument. The opposite or proximal end of the hand-held cover or casing 22 mates with a flexible material conduit 21 which serves to encase conduits and elongated electrical cable structures serving to operatively interconnect the hand piece 12 to the refrigerant control valve body generally indicated as 24.

The evaporator body 20 is preferably formed of copper and is threaded on the proximal or supply end for mating engagement with supply line sealing nut 25. The nut 25 has a plurality, preferably four, axial holes 27 on its outer perimeter to allow air or like fluid to pass from the back or supply side of the nut to the front side thereof through spacing chamber 26 about the exterior of the evaporator body surface and the interior evaporator chamber 28. A sealing gasket 29 or like sealing member serves to insure fluid sealing engagement between the proximal or supply end of the evaporator body 20 and nut 25.

A plurality of slots or openings, preferably four, indicated as 30 are formed in the end cap 16 and are disposed in contiguous relation to the extremity of the distal end of evaporator body 20. These slots 30 communicate with the spacing chamber 26 and allows the exiting of the air, gas or atomized fluid from the hand piece onto the tissue surrounding or involved in the surgical or treatment site. Due to the disposition and configuration of the spacing chamber 26, the air or fluid has its temperature reduced greatly because of the direct contact with the exterior surface of the evaporator body 20 prior to exiting the hand piece 12 through the plurality of slots 30.

A plastic sleeve 32 fits inside the proximally disposed bore of the outer casing 22 and forces the nut 25 to bottom in the stepped rear bore of the plastic case or casing 22 as shown in FIG. 3. Rigid material pin 33 passes through the casing 22 and sleeve 32 and is positioned to secure the evaporator body 20 within the interior of the casing 22 by means of the securing nut 25.

The rear of sleeve 16 includes an axially disposed air passage 34 serving to channel the forced flow of air or like gases from the interior of the flexible material conduit 21, as from chamber 35 into sub-chamber 36 and through slots 27 in nut 25 into the spacing 26, where the air comes in contact with the evaporator body 20. As set forth above, the air then eventually exits through the slots 30 onto the tissue of the treatment site of the patient.

Refrigerant in liquid form is supplied to the hand piece 12 generally and in particularly to the interior of evaporator chamber 28 of evaporator body 20 by an elongated refrigerant conduit 34. The opposite end of the refrigerant conduit 24 is secured within the valve body 24 and will be explained in greater detail hereinafter. However, after the refrigerant exits conduit 34 it is evaporated, causing a reduction in temperature. The evaporated refrigerant then passes from the chamber 28 back to the valve body 24 through return conduit 38. One end of the return conduit 38 is located in direct communicating relation with the proximal end of the evaporator body 20 and is secured therein by engagement within the interior of the central bore or channel of the nut 25. Accordingly, it is seen that the refrigeration assembly of the present invention is essentially a closed cycle, micro-refrigeration system as will be explained in even greater detail hereinafter.

The outer flexible material conduit 21 further serves to house coaxial epilator power supply cable 40 wherein one end of the cable 40 associated with the hand piece 12 passes through sleeve 32. An inner conductor of power supply cable 40 is soldered to a projecting lug 41 within sleeve 38, the lug 41 is a part of the clamping nut 25.

A temperature control sensing thermistor 43 is connected to the exterior of the refrigerant return conduit 38 and serves to interconnect this conduit 38 with shielded electrical conductor 42. Electrical conductor 42 has its opposite end connected to a temperature control assembly 45 (see FIG. 4). Naturally, the length of the conductor 42 passes along the length of the interior of the outer protective conduit 21 as shown in FIG. 3.

As generally represented at 47, the outer casing 21 is sealed to one end of the valve body 24 and thereby defines an air tight conduit through which air is delivered from delivery conduit 49 associated with the cabinet and to which the air or atomized fluid is forced after being sterilized and otherwise treated. An axial passage 49' serves to interconnect in fluid communication the interior of the flexible material conduit or casing 21 with the air supply conduit 49. In addition, while the length of the connecting and enclosing conduit 21 may be variable, a preferred length is approximately 6 feet so as to give the surgeon ample room to maneouver and properly position the hand piece 12 during medical treatment.

As set forthabove, the refrigerant line 34 has its distal end delivering liquid refrigerant to the interior evaporator chamber 28. The proximal end of refrigerant line 34 is associated and secured to valve body 24 by means of sealing nut 52 secured to the extremity, which is threaded, of one end of the control valve body 24 as at 24'. Sealing means 53 is provided to insure a fluid tight seal as indicated.

The liquid refrigerant or freon flow control valve 24 is particularly designed to accommodate the extremely low freon flow rate needed in the practice of the subject invention. Capillary tubes commonly used in prior art devices could not be used herein because the oil used to lubricate the freon compressor would carry over into the liquid freon and clog the small capillary orifice at the evaporator thereby reducing gas flow.

The valve body generally indicated as 24 operates as follows: The referigerant or freon in liquid form passes up through line 55 and in through passage 56 formed in the portion 24' of the valve body itself. The freon is forced through lines 55 and 56 after leaving the compressor and condensor mechanism associated with the fluid control assembly generally indicated as 100 which will be described in greater detail hereinafter. After passing through line 56 in valve body portion 24', the liquid freon enters chamber 57 which is in direct communication with the needle valve structure 59. In the position shown in FIG. 3, the needle valve 59 is closed by engaging valve seat 60 thereby preventing freon flow out through valve chamber 62 passed filter structure 61. At this point, the liquid freon is forced to enter into the correspondingly positioned end of the refrigerant conduit or line 34. The refrigerant is then forced under fluid flow pressure to the opposite end of the conduit 34 where it empties into the interior of evaporator chamber 28 and evaporates cooling the evaporator body 20. The liquid freon evaporates a essentially 0 PSI gage pressure, and as set forth above, effectively reduces the temperature of evaporator body 20 and any fluid coming in contact therewith as by passing through spacing chamber 26. In a preferred embodiment, the refrigerant line or conduit 34 has an outside diameter of 0.030 inches and an interior diameter of 0.010 inches and is made from a Teflon material and further defines the system of the present invention as being a closed cycle, micro-refrigerant system.

The opposite portion 24" of the valve body 24 houses the thermally activated valve which controls flow of liquid refrigerant into the refrigerant conduit 34 through the displacement of valve head 59 relative to valve seat 60. More specifically, displacement of valve head 59 occurs due to the thermal expansion of the expansion element 62. The expansion element 62 is made from lead and is soldered to a brass material valve head 59. The upper end of the expansion element 62 is soldered to the threaded valve stem 64 which is threadedly connected to the upper valve housing 24" and sealed thereto by a sealing or packing nut 65 and sealing ring 66.

The upper valve body portion 24" is sealed to the lower body 24' by an O-ring or like sealing structure 67. The valve head 59 is opened and closed by electric power applied to heater element 69 thermally bonded to the expansion section 71 forming part of the valve stem assembly. Conducting wires 70 are brought out of the valve stem 64 through slot 72. Initial manual adjustment of the valve is made by turning valve stem 64 by a screwdriver applied to slot 73 or like tools.

The vaporized gas leaving evaporator chamber 28 passes through tubing 38 into valve body 24 to the low side of the freon compressor 74. The high side of the compressor 74 passes high pressure hot gas through line 76 into the cooled condensor 79 cooled by fan 78. The condensed gas or liquid gas is then passed through level sight glass 80 and sequentially through line 81 to a reservoir 82 and through strainer dryer 84 to the branch or tee 86 dividing liquid freon or refrigerant into two supply branches. One of the lines 55 extends through to line which feeds the control valve 24 and line 88 through strainer dryer 8 through capillary restriction tube 91 and into the heat exchanger tube 123 of the air dehydrator unit 120. The liquid refrigerant continues to flow through this exchanger into line 94 to line 95 to the low suction side of the freon compressor 74.

Atmospheric air or treated gases enter filter 102 through opening 98 and through tee divider line 111 into the suction side of air compressor 101. Compressed air leaves air compressior 101 through line 103 into tee dividing line 112. Line 105 from this tee directs the gas to pressure gauge 106. The other side of the tee 112 is directed to tee 114 and then to adjustable air pressure release valve 107. The excess air is retained via line 109 back into the suction side of the air compressor 101 at tee dividing line 111.

Air enters from tee 114 to an air sterilizer 110 where the air is heated to approximately 800° F. in a heat recovery type heat exchanger. Air enters chamber 116 where heating is done. It then passes to chamber 115 where the heat applied in chamber 116 is transferred back to chamber 116. The air then passes from chamber 115 through line 117 into the atmospheric cooler coil 119, then to line 119 into the dehydrator 120 and cavity 121. At this point, almost all moisture is frozen out of the air and such moisture freezes and clings to the cold exchanger tubes 123.

Figure 4:
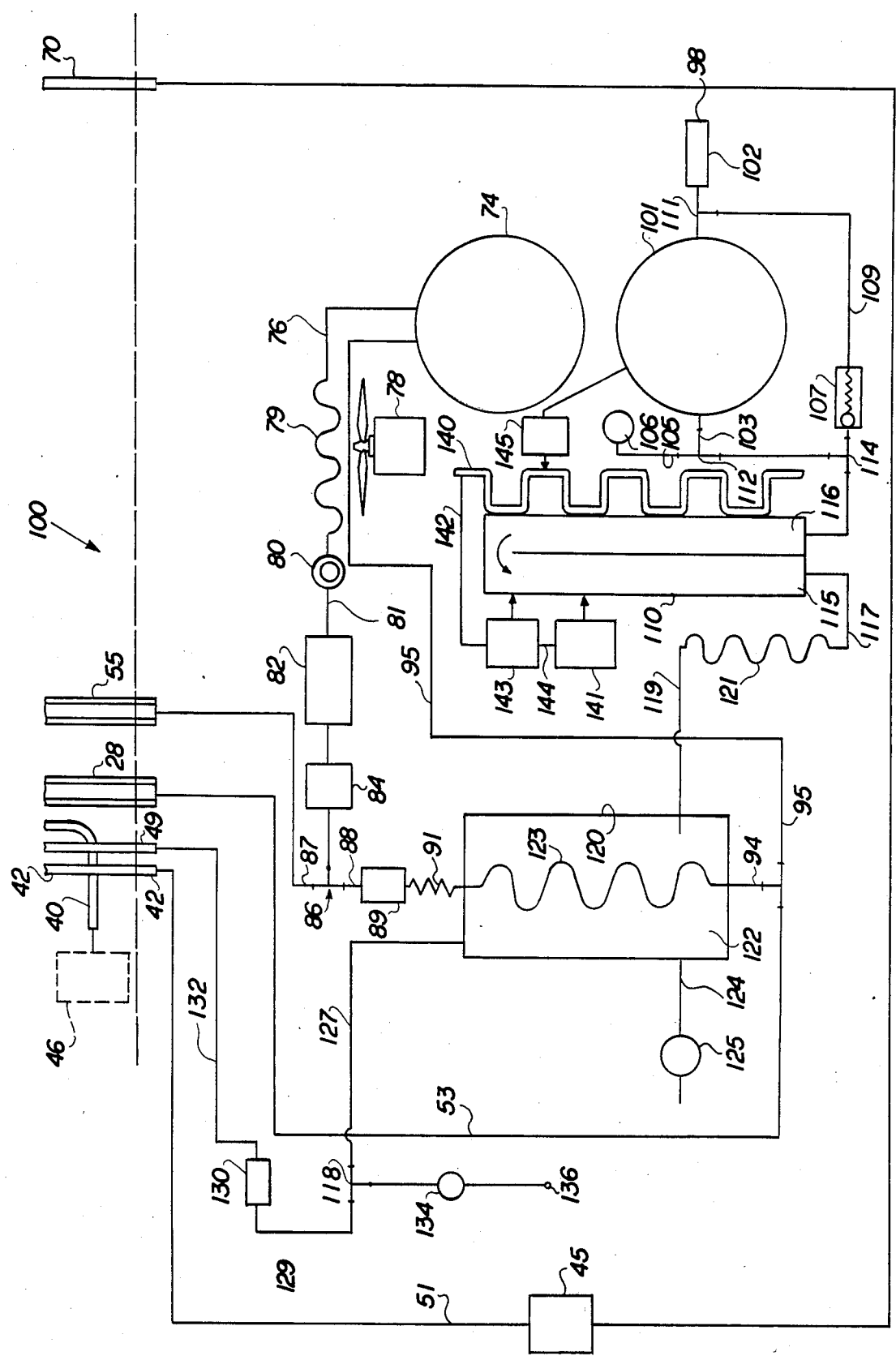
FIG. 4 is a schematic representation of interior components of the cabinet structure to which the hand piece is directed and from which refrigerant is received as well as air, gases, or treated atomized fluid.

Not shown in the diagram of FIG. 4 is an electrical heater element and temperature control sensor thermally bonded to these tubes and connected to a temperature controller. This structure could serve to maintain the exchanger surface temperature at any desired level to provide and control the humidity level.

A water drain line 124 is connected to drain valve 125 to drain water melted from the dehydrator coil after they have warmed up by activation of the thermally controlled sensor assembly as described immediately above.

Line 127 connected to dehydrator cavity 122 allows the dehydrated sterile air to be supplied to tee dividing line 118, to line 129 and to flow meter 130. The air continues from flow meter to line 132 to the air supply tube 49 leading to the interior of protective flexible material casing 21 and eventually to the hand piece.

Connected to tee 118 is valve 134 whose supply 136 can be treated gas or atomized medication in fluid form.

The coaxial line 42 connects the epilator equipment 46 to energize the treatment needle 14 or other surgical instrumentation connected to the chuck 19 at the end of evaporator body 20. (See FIG. 3.).

The sterilizer heater element 140 is in physical and thermal contact with the exchanger elements 116 and 115 and is temperature controlled by sensor 141. This is coupled to high limit thermal switch 143 by line 144 through line 142 to the heater element 140. In contact with the heating element 140 is thermal switch 145 which closes when the heater temperature reaches 800° F. and starts the air compressor 101. This prevents unsterilized air from reaching the treatment site of the patient.

It is therefore to be understood that the following claims are intended to cover all of the generic and specific features of the invention herein described, and all statements of the scope of the invention which as a matter of language, might be said to fall therebetween.

Now that the invention has been described,
What is claimed is:

1. A tissue treatment assembly of the type primarily designed to blanket a treatment site and adjacent tissue with a continuation flow of reduced temperature air or atomized treatment fluid, said assembly comprising:
   (a) a fluid control assembly including a housing connected to and located remotely from a hand assembly, said hand assembly including a hand piece structured for support by a hand of the user and manipulation thereby relative to the treatment site,
   (b) conduit means having an elongated configuration andd attached substantially at opposite ends thereof to said hand piece and said fluid control assembly for establishing fluid flow therebetween,
   (c) a refrigerator assembly including an evaporator of sufficient dimension to be mounted in said hand piece in heat transferring relation to a flow of air issuing from said hand piece onto the treatment site; said refrigerator assembly further including a refrigerant compressor and condensor dimensioned to define micro-refrigerant components of said refrigerator assembly and being mounted in said fluid control assembly and connected in substantially closed fluid communication with said evaporator via said conduit means,
   (d) said refrigerator assembly comprising a liquid refrigerant conduit mounted to extend along the length of said conduit means and including one end disposed in fluid receiving relation to said valve means and an opposite end disposed in fluid delivering relation to said evaporator,
   (e) a return conduit mounted within said conduit means and extending along the length thereof, said return conduit having one end disposed in fluid receiving communication with said evaporator chamber and an opposite end connected to said fluid control assembly in fluid delivering communication with said refrigerator compressor,
   (f) an air supply assembly mounted in said control assembly and including an air inlet from a conventional source and an air compressor means connected to said air inlet for compressing received air and directing air flow via said conduit means to said hand piece,
   (g) a sterilizer assembly mounted in said fluid control assembly and connected in fluid receiving relation to said air compressor, sterilizedd air directed therefrom to a remainder of said fluid control assembly and to said evaporator via said conduit means,
   (h) a valve means for regulating fluid flow of liquid refrigerant from said fluid control assembly to said evaporator via said conduit means, and
   (i) a temperature control assembly operatively interconnected to said valve means for activation thereof and including a sensor assembly disposed to sense temperature of said evaporator, said valve means actuated to establish liquid refrigerant flow to said evaporator upon the sensing of a predetermined temperature of said evaporator.

2. An assembly as in claim 1 wherein said hand piece comprises a substantially elongated configuration and a cover portion extending along a length of said hand piece in substantially surrounding relation to said evaporator; a cooling chamber disposed between said evaporator and said cover and further disposed in air receiving communication with said fluid control assembly via said conduit means, said cooling chamber interconnected in fluid communication with the exterior of said hand piece at a free end thereof.

3. An assembly as in claim 2 wherein said hand piece further comprises channel means formed in said free end thereof for directing air collected and cooled in said cooling chamber outwardly therefrom into blanketing relation to the treatment site.

4. An assembly as in claim 3 further comprising a cap structure secured to said free end and structured to at least partially define said channel means, said cap structure removably secured to said free end of said hand piece.

5. An assembly as in claim 4 wherein said cap structure is constructed to allow passage therefrom of a surgical instrument, said channel means substantially surrounding said instrument whereby said instrument is cooled by direct contact with said evaporator.

6. An assembly as in claim 4 wherein said cap structure comprises an air directing means secured thereto and projecting outwardly therefrom and structured for confining the treatment site and applying a positive pressure zone of temperature controlled sterile fluid over the treatment site.

7. An assembly as in claim 1 wherein said evaporator comprises a distal end disposed adjacent a free end of said hand piece and structured to removably engage a surgical instrument thereon, said distal end disposed and structured to project the surgical instrument outwardly from said free end of said hand piece for engagement with the treatment site.

8. An assembly as in claim 1 wherein said fluid control means further comprises a supply of treated fluid commonly interconnected in fluid communication to said hand piece with an air supply from said air compressor via said conduit means.

9. An assembly as in claim 8 wherein said treated fluid comprises medicated fluid in atomized form.

10. An assembly as in claim 1 wherein said fluid control means further comprises dehumidifier means disposed in air receiving relation to said sterilizer assembly and disposed and structured to direct dehydrated air therefrom to said hand piece via said conduit means.

11. An assembly as in claim 1 wherein said sterilizer assembly comprises a heater structure disposed in heat transferring relation to air passing through said sterilizer assembly, said heater structure constructed and activated to heat the flow of air received from said air compressor to a sufficiently high temperature to sterilize the air.

12. A tissue treatment assembly of the type primarily designed to blanket a treatment site and adjacent tissue with a continuous flow of reduced temperature air or atomized treatment fluid, said assembly comprising:
(a) a fluid control assembly including a housing connected to and located remotely from a hand assembly, said hand assembly including a hand piece structured for support by a hand of the user and manipulation thereby relative to the treatment site,
(b) conduit means having an elongated configuration and attached substantially at opposite ends thereof to said hand piece and said fluid control assembly for establishing fluid flow therebetween,
(c) a refrigerator assembly including an evaporator of sufficient dimension to be mounted in said hand piece in heat transferring relation to a flow of air issuing from said hand piece onto the treatment site; said refrigerator assembly further including a refrigerant compressor and condensor dimensioned to define micro-refrigerant components of said refrigerator assembly and being mounted in said fluid control assembly and connected in substantially closed fluid communication with said evaporator via said conduit means,
(d) an air supply assembly mounted in said control assembly and including an air inlet from a conventional source and an air compressor means connected to said air inlet for compressing received air and directing air flow via said conduit means to said hand piece,
(e) a sterilizer assembly mounted in said fluid control assembly and connected in fluid receiving relation to said air compressor, sterilized air directed therefrom to a remainder of said fluid control assembly and to said evaporator via said conduit means,
(f) an air delivery conduit mounted to extend along the length of aid conduit means and connected at one end to a cooling chamber within said hand piece and an opposite end of said delivery conduit connected to said fluid control assembly in fluid receiving relation to said air compressor and said sterilizer assembly downstream thereof,
(g) a valve means for regulating fluid flow of liquid refrigerant from said fluid control assembly to said evaporator via said conduit means, and
(h) a temperature control assembly operatively interconnected to said valve means for activation thereof and including a sensor assembly disposed to sense temperature of said evaporator, said valve means actuated to establish liquid refrigerant flow to said evaporator upon the sensing of a predetermined temperature of said evaporator.

13. An assembly as in claim 12 wherein said cooling chamber is mounted within said hand piece and extends along the length of said evaporator exteriorly thereof, said cooling chamber disposed to cool fluid therein by heat exchange with said evaporator.

14. An assembly as in claim 13 further comprising delivery channel means formed in a free end of said hand piece in fluid directing relation between said cooling chamber and the exterior of said hand piece.

15. An assembly as in claim 14 wherein said channel means comprises a plurality of channels collectively disposed and dimensioned to direct a flow of air from said cooling chamber onto the treatment site.

16. An assembly as in claim 1 wherein said evaporator comprises an evaporator chamber formed on the interior thereof and extending along a major length thereof, said liquid refrigerant conduit disposed and structured to empty liquid refrigerant into said evaporator chamber for evaporation thereof, whereby said evaporator is cooled, said valve atuation means positionable into an open position for delivery of liquid refrigerant to said evaporator.

* * * * *